United States Patent
Weyer et al.

(12)

(10) Patent No.: US 6,245,954 B1
(45) Date of Patent: Jun. 12, 2001

(54) METHOD OF PRODUCING ALKYL CHLORIDE, ALKENYL CHLORIDE AND ALKINYL CHLORIDE

(75) Inventors: Hans-Jürgen Weyer, Bobenheim-Roxheim; Armin Stamm, Mainz; Theodor Weber, Ludwigshafen; Jochem Henkelmann, Mannheim, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/700,746
(22) PCT Filed: May 21, 1999
(86) PCT No.: PCT/EP99/03489
   § 371 Date: Nov. 20, 2000
   § 102(e) Date: Nov. 20, 2000
(87) PCT Pub. No.: WO99/62848

PCT Pub. Date: Dec. 9, 1999

(30) Foreign Application Priority Data

Jun. 4, 1998 (DE) .............................. 198 24 929

(51) Int. Cl.$^7$ ........................... C07C 17/16; C07C 17/02
(52) U.S. Cl. ........................................... 570/267; 570/217
(58) Field of Search ..................................... 570/261, 217

(56) References Cited

U.S. PATENT DOCUMENTS 5,241,086 * 8/1993 Mas ...................................... 570/261
5,384,415 * 1/1995 Mas ...................................... 570/261

* cited by examiner

*Primary Examiner*—Alan Siegel
(74) *Attorney, Agent, or Firm*—Keil & Weinakuf

(57) ABSTRACT

The present invention relates to a process for preparing alkyl, alkenyl and alkynyl chlorides from alcohols by reaction with a chlorinating agent in the presence of a catalyst, wherein the catalyst is a urea compound.

5 Claims, No Drawings

METHOD OF PRODUCING ALKYL CHLORIDE, ALKENYL CHLORIDE AND ALKINYL CHLORIDE

This application is a 371 of PCT/EP99/03489 filed May 21, 1999.

The present invention relates to a novel process for preparing alkyl, alkenyl and alkynyl chlorides by reacting alcohols with chlorinating agents in the presence of urea compounds. Alkyl, alkenyl and alkynyl chlorides are known and are suitable as valuable intermediates for organic syntheses. They are obtained in known processes by reacting alcohols with phosgene in the presence of catalysts.

Thus, GB-A 2 182 039 discloses a process for preparing alkyl chlorides from alcohols by reaction with phosgene in the presence of triarylphosphine oxides or triarylphosphine sulfides as catalysts. EP-A 514 683 proposes aliphatic phosphorus compounds as catalysts.

EP-A-200403 discloses the halogenation of alkoxy compounds in the presence of unsubstituted urea.

The disadvantage of these processes is that they result in phosphorus-containing distillation residues which are difficult to dispose of owing to the formation of phosphoric acids.

It is an object of the present invention to remedy the abovementioned disadvantage and, in particular, to provide a process for preparing alkyl, alkenyl and alkynyl chlorides which makes do with small amounts of catalyst and substantially avoids the formation of byproducts.

We have found that this object is achieved by a process for preparing alkyl, alkenyl and alkynyl chlorides from alcohols by reaction with a chlorinating agent in the presence of a catalyst, wherein the catalyst is a urea compound of the formula (I)

$R^1R^2N\text{—}CX\text{—}NR^3R^4$ (I), in which the radicals $R^1$, $R^2$, $R^3$ and $R^4$ can be identical or different, are, independently of one another, optionally mono- to tri-$C_1$–$C_4$-alkoxy-, $C_2$–$C_4$-acyl-, $C_2$–$C_4$-acyloxy-, phenoxy-, $C_2$–$C_8$-dialkylamino-, halo-, nitro- and/or cyano-substituted $C_1$–$C_{20}$-alkyl, $C_2$–$C_{12}$-alkenyl, $C_2$–$C_{12}$-alkynyl or optionally mono- to tri-$C_1$–$C_4$-alkyl-, $C_1$–$C_4$-alkoxy-, $C_2$–$C_4$-acyl-, $C_2$–$C_4$-acyloxy-, phenoxy, $C_2$–$C_8$-dialkylamino-, halo-, nitro- and/or cyano-substituted $C_3$–$C_{12}$-cycloalkyl, $C_4$–$C_{12}$-alkylcycloalkyl, $C_4$–$C_{12}$-cycloalkylalkyl, heterocycloalkyl, $C_5$–$C_{20}$-heterocycloalkylalkyl, $C_6$–$C_{14}$-aryl, $C_7$–$C_{20}$-arylalkyl or $C_7$–$C_{20}$-alkylaryl, or in which one of the radicals $R^1$ or $R^2$ can be, together with one of the radicals $R^3$ or $R^4$, an optionally mono- to tri-$C_1$–$C_4$-alkyl-, $C_1$–$C_4$-alkoxy-, $C_2$–$C_4$-acyl-, $C_2$–$C_4$-acyloxy-, phenoxy-, $C_2$–$C_8$-dialkylamino-, halo-, nitro- and cyano-substituted $C_2$–$C_{12}$-alkylene chain which may be interrupted by an ether, thioether, tertiary amino, keto, lactone, N-alkyl-substituted lactam or sulfone moiety, and in which X is an oxygen or sulfur atom, and/or a urea compound of the general formula II

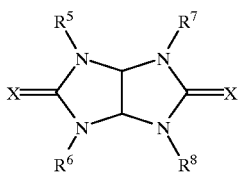

(II)

in which X has the stated meaning, and $R^5$, $R^6$, $R^7$ and $R^8$ can be identical or different and, independently of one another, have the meaning given for $R^1$ to $R^4$
and/or
a compound of the general formula (III),

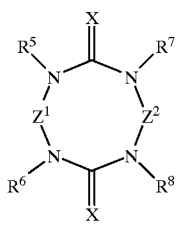

(III)

in which X, $R^5$ to $R^8$ have the abovementioned meanings and $Z^1$, $Z^2$, which may be identical or different, are an optionally mono- to tri-$C_1$–$C_4$-alkyl-, $C_1$–$C_4$-alkoxy-, $C_2$–$C_4$-acyl-, $C_2$–$C_4$-acyloxy-, phenoxy-, $C_2$–$C_8$-dialkylamino-, halo-, nitro- and/or cyano-substituted methylene, ethylene or vinylene group.

The organic substituents $R^1$ to $R^8$ in the compounds I, II and III have the following meanings independently of one another:

$C_1$–$C_{20}$-alkyl, preferably $C_1$–$C_{12}$-alkyl, particularly preferably $C_1$–$C_8$-alkyl such as methyl, ethyl, n-propyl, isopropyl, n-butyl, isobutyl, sec-butyl, tert-butyl, n-pentyl, isopentyl, n-hexyl, isohexyl, n-heptyl, isoheptyl, n-octyl and isooctyl, especially $C_1$–$C_4$-alkyl such as methyl, ethyl, n-propyl, isopropyl, n-butyl, isobutyl, sec-butyl and tert-butyl, $C_2$–$C_{12}$-alkenyl, preferably $C_2$–$C_8$-alkenyl, such as vinyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethylpropenyl, 1-ethyl-1-propenyl, 1-ethyl-2-propenyl, 1-hexenyl, 2-hexenyl, 3-hexenyl, 4-hexenyl, 5-hexenyl, particularly preferably vinyl, 2-propenyl and 1-butenyl, $C_2$–$C_{12}$-alkynyl, preferably $C_2$–$C_8$-alkynyl, such as ethynyl, 1-propynyl, 2-propynyl, 1-butynyl, 3-butynyl, 1-methyl-2-propynyl, 1-pentynyl, 2-pentynyl, 3-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, particularly preferably ethynyl, 1-propynyl and 1-butynyl.

Said groups may be substituted by $C_1$–$C_4$-alkoxy, $C_2$–$C_4$-acyl, $C_2$–$C_4$-acyloxy, phenoxy, $C_2$–$C_8$-dialkylamino, halogen, nitro and/or cyano. Substituted alkyl radicals are preferred, and alkyl radicals substituted by halogen or cyano, such as cyanomethyl, chloromethyl, are particularly preferred.

$R^1$ to $R^8$ are also:

$C_3$–$C_{12}$-cycloalkyl, preferably $C_5$–$C_8$-cycloalkyl such as cyclopentyl, cyclohexyl, cycloheptyl and cyclooctyl, particularly preferably cyclopentyl and cyclohexyl, $C_4$–$C_{12}$-alkylcycloalkyl, preferably $C_5$–$C_{10}$-alkylcycloalkyl, particularly preferably $C_5$–$C_8$-alkylcycloalkyl, $C_4$–$C_{12}$-cycloalkylalkyl, preferably $C_5$–$C_{10}$-cycloalkylalkyl, particularly preferably $C_5$–$C_8$-cycloalkylalkyl, $C_5$–$C_{20}$-alkylcycloalkylalkyl, preferably $C_6$–$C_{16}$-alkylcycloalkylalkyl, particularly preferably $C_7$–$C_{12}$-alkylcycloalkylalkyl, heterocycloalkyl such as a 5- or 6-membered ring with one or two O, N and/or S atoms in the ring, which may be aromatic or nonaromatic, such as 2- or 3-furyl, 2- or 3-thienyl, 2- or 3-pyrrolyl, 2- or 4-imidazolyl, 2- or 4-oxazolyl, 2- or 4-thiazolyl, pyridinyl, morpholyl, thiomorpholyl and pyrazolyl, $C_6$–$C_{14}$-aryl such as phenyl, 1-naphthyl and 2-naphthyl, preferably phenyl, $C_7$–$C_{20}$-alkylaryl, preferably $C_7$–$C_{16}$-alkylaryl, particularly preferably $C_7$–$C_{12}$-alkylphenyl such as 2-methylphenyl, 3-methylphenyl, 4-methylphenyl, 2-ethylphenyl, 3-ethylphenyl and 4-ethylphenyl, $C_7$–$C_{20}$-arylalkyl, preferably $C_7$–$C_{16}$-aralkyl, particularly preferably $C_7$–$C_{12}$-phenylalkyl such as benzyl, 1-phenylethyl, 2-phenylethyl, 3-phenylpropyl, 1-phenylbutyl, 2-phenylbutyl, 3-phenylbutyl, 4-phenylbutyl, particularly preferably benzyl, 1-phenylethyl and 2-phenylethyl.

Said groups can be substituted by $C_1$–$C_4$-alkyl, $C_1$–$C_4$-alkoxy, $C_2$–$C_4$-acyl, $C_2$–$C_4$-acyloxy, phenoxy, $C_2$–$C_8$-dialkylamino, halogen, nitro and/or cyano.

Urea compounds of the formulae I, II or III which are preferably used are those which are liquid under the reaction conditions, particularly preferably N,N'-dimethylethyleneurea, N,N'-dimethylpropyleneurea, N,N,N',N'-tetrabutylurea and N,N,N',N'-tetramethylthiourea, N-chloromethyl-N'-cyanomethylpropyleneurea, N-methyl-N'-ethylpropyleneurea, 1,3-dimethyl-1,3-dihydrobenzimidazol-2-one, 1-methyl-3-phenylimidazolidine-2,4,5-trione, 1,3,4,6-tetramethyl-1,3,4,6-tetrahydroimidazo[4,5-d]imidazole-2,5-dione and 4-methoxy-1-methyl-3-phenylimidazolidine-2-thione.

Said urea compounds can be employed as such, in the form of their salts with hydrohalic acids, for example as hydrochlorides, or in the form of their salts obtainable by reaction with phosgene (Vilsmeier salts).

Alcohols suitable for use according to the invention are mainly those of the formula

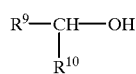

(IV)

in which $R^9$ and $R^{10}$ can be identical or different and are hydrogen, alkyl, alkenyl, alkynyl, alkoxy, aryloxy, hydroxyalkyl, hydroxyalkenyl or hydroxyalkynyl groups.

Among the alcohols complying with the definition, those preferred in relation to the required products of the process are those in which the $R^9$ and $R^{10}$ radicals have the following meaning:

hydrogen, $C_1$–$C_{22}$-alkyl, preferably $C_4$–$C_{18}$-alkyl, among these preferably $C_6$–$C_{10}$-alkyl such as, in particular n-hexyl and n-octyl;

$C_3$–$C_{22}$-alkenyl, preferably $C_4$–$C_6$-alkenyl such as, in particular, butenyl;

$C_3$–$C_{22}$-alkynyl, preferably $C_3$–$C_8$-alkynyl such as, in particular, propynyl;

$C_1$–$C_{22}$-alkoxy, preferably $C_1$–$C_4$-alkoxy such as, in particular, propoxy;

mono- or binuclear aryloxy such as, preferably, phenyloxy, it being possible for the aromatic rings to contain heteroatoms such as oxygen, sulfur or nitrogen and/or to be substituted by up to three $C_1$–$C_{12}$-alkyl groups, halogen such as fluorine, chlorine and bromine or $C_1$–$C_4$-alkoxy groups;

$C_1$–$C_{16}$-hydroxyalkyl, preferably $C_2$–$C_{12}$-hydroxyalkyl, and among these preferably $C_4$–$C_8$-hydroxyalkyl such as, in particular, hydroxybutyl, hydroxyhexyl and hydroxyoctyl;

$C_3$–$C_{16}$-hydroxyalkenyl, preferably $C_3$–$C_{12}$-hydroxyalkenyl, and among these preferably $C_4$–$C_8$-hydroxyalkenyl such as, in particular, hydroxybutenyl, hydroxyhexenyl and hydroxyoctenyl;

$C_3$–$C_{16}$-hydroxyalkynyl, preferably $C_3$–$C_{12}$-hydroxyalkynyl and among these preferably $C_4$–$C_8$-hydroxyalkynyl such as, in particular, hydroxybutynyl, hydroxyhexynyl and hydroxyoctynyl.

These radicals, apart from hydrogen, may in turn be substituted by, preferably, $C_1$–$C_4$-alkyl, $C_1$–$C_4$-ester, cyano, halogen such as, in particular, fluorine, chlorine and bromine, aryl such as, in particular, phenyl and 4-methoxyphenyl, and aryloxy such as, preferably phenyloxy.

Preferred alcohols are:

2-(4-methoxyphenyl)ethanol 2-ethylhexanol n-octanol 3-butenol propynol 1,4-butanediol 1,8-octanediol, and 1,6-hexanediol is particularly preferred in relation to the required products of the process.

Chlorinating agents which can be employed are reagents known per se, such as phosgene, thionyl chloride and oxalyl chloride, and the use of phosgene is preferred.

It is often advantageous additionally to use hydrogen chloride, in particular in amounts of from 5 to 100 mol %, preferably 20 to 40 mol %, of the alkohol.

The process according to the invention can be carried out as homogeneously catalyzed liquid-phase reaction. Suitable as liquid reaction medium are the primary, secondary or tertiary alcohols to be employed or an inert solvent or mixtures thereof. Suitable inert solvents are aromatic hydrocarbons such as toluene, xylene or benzene, halogenated hydrocarbons such as trichloroethane, chlorobenzene or dichlorobenzene, or esters such as ethyl acetate or butyl acetate.

The process according to the invention can be carried out continuously or batchwise. The process according to the invention is preferably carried out continuously, for example in a stirred vessel, in a cascade of stirred vessels, in a loop reactor or in a countercurrent column. The reaction temperature is generally from −20 to 180° C., preferably 0 to 120° C., particularly preferably 40 to 100° C. The reaction is generally carried out under pressures from 0.01 to 50 bar, preferably 0.5 to 5 bar, particularly preferably under atmospheric pressure.

The urea compound I, II and/or III is generally employed in amounts of from 0.01 to 20 mol %, based on the amount of the alcohol (IV) employed. The amount of the catalyst also depends on whether the reaction is carried out just in the alcohol employed or in the presence of a solvent.

The amount of urea compound I, II and/or III used is preferably between 0.001 and 1 mol %, particularly preferably between 0.002 and 0.1 mol %, particularly preferably between 0.005 and 0.05 mol %.

The molar ratio between the chlorinating agent and the alcohol (IV) is generally from 0.5:1 to 50:1. An excess of chlorinating agent will normally be used since, otherwise, unreacted alcohol remains. The molar ratio between the alcohol. The mixture was then kept at the reaction temperature for a further hour. Excess phosgene was then driven out of the mixture with nitrogen, and the crude product obtained in this way was, after a clarifying filtration, investigated by gas chromatography.

Details of these experiments are to be found in Table 1 below.

EXAMPLE 6

At a temperature of 120–130° C., b mol of thionyl chloride and 2 mol of 1,4-butanediol were added over the course of 7 hours to a mixture of 0.5 mol of 1,4-dichlorobutane and 0.001 mol % of N,N'-dimethylpropyleneurea, based on 1,4-butanediol. The mixture was then kept at this reaction temperature for a further hour. Excess thionyl chloride was then driven out of the mixture with nitrogen, and the crude product obtained in this way was, after a clarifying filtration, investigated by gas chromatography.

Details of the experiment are to be found in Table 1 below.

TABLE 1

| | | | | GC Analysis [%] | | |
| Example | Alcohol | Urea compound | Chlorinating agent b [mol] | Alkyl chloride | Alcohol | Chloroformate |
| --- | --- | --- | --- | --- | --- | --- |
| 1 | 1,4-Butanediol | N,N'-Dimethylpropyleneurea | COCl$_2$/1.05 | 98.6 | <0.01 | <0.01 |
| 2 | 1,4-Butanediol | N,N,N',N'-Tetrabutylurea | COCl$_2$/1.05 | 95.6 | <0.01 | 0.26 |
| 3 | 1,4-Butanediol | N,N'-Dimethylethyleneurea | COCl$_2$/1.05 | 98.6 | <0.01 | <0.01 |
| 4 | 1,4-Butanediol | N,N,N',N'-Tetramethylthiourea | COCl$_2$/1.05 | 98.3 | <0.00 | <0.04 |
| 5 | 1,4-Hexanediol | N,N'-Dimethylpropyleneurea | COCl$_2$/1.05 | 98.2 | 0.02 | <0.01 |
| 6 | 1,4-Butanediol | N,N'-Dimethylpropyleneurea | SOCl$_2$/1.05 | 98.4 | <0.01 | <0.01 | chlorinating agent and the alcohol (IV) is preferably 1:1 to 2:1, particularly preferably 1:1 to 1.5:1, in particular 1:1 to 1.2:1.

The chlorination reaction can be followed by one or more steps for purifying the reaction product. Thus, where appropriate, the liquid discharged from the phosgenation reaction can have insoluble impurities removed by a mechanical separation such as a clarifying filtration. Such a mechanical separation step is often sufficient to obtain a product of sufficiently high purity, and further processing can be dispensed with. However, further purification steps to remove soluble impurities, for example by distillation or recrystallization, may follow.

The catalyst-containing distillation residue can be returned to the reaction.

The alkyl, alkenyl and alkynyl chlorides obtainable in an economic manner by the process according to the invention are well known to be valuable intermediates for organic syntheses, in particular for crop protection agents, electrochemical auxiliaries and plastics precursors.

The invention is illustrated by the following examples.

EXAMPLES 1 TO 5

At a temperature of 120–130° C., b mol of phosgene and 2 mol of the alcohol (IV) were added over the course of 5 hours to a mixture of 0.5 mol of the particular alkyl chloride and 0.001 mol % of the urea compound, based on the

We claim:

1. A process for preparing alkyl, alkenyl and alkynyl chlorides from alcohols of the formula IV

(IV)

In which $R^9$ and $R^{10}$ are hydrogen, alkyl, alkenyl, alkynyl, alkoxy, aryloxy, hydroxyalkyl, hydroxyalkenyl or hydroxyalkynyl groups, by reaction with a chlorinating agent in the presence of a catalyst, wherein the catalyst is a urea compound of the formula (I)

in which the radicals $R^1$, $R^2$, $R^3$ and $R^4$ can be identical or different, are, independently of one another, optionally mono- to tri-$C_1$–$C_4$-alkoxy-, $C_2$–$C_4$-acyl-, $C_2$–$C_4$-acyloxy-, phenoxy-, $C_2$–$C_8$-dialkylamino-, halo-, nitro- and/or cyano-substituted $C_1$–$C_{20}$-alkyl, $C_2$–$C_{12}$-alkenyl, $C_2$–$C_{12}$-alkynyl or optionally mono- to tri-$C_1$–$C_4$-alkyl-, $C_1$–$C_4$-alkoxy-, $C_2$–$C_4$-acyl-, $C_2$–$C_4$-acyloxy-, $C_2$–$C_8$-dialkylamino-, halo-, nitro- and/or cyano-substituted $C_3$–$C_{12}$-cycloalkyl, $C_4$–$C_{12}$-alkylcycloalkyl, $C_4$–$C_{12}$-cycloalkylalkyl, heterocycloalkyl, $C_5$–$C_{20}$-heterocycloalkylalkyl, $C_6$–$C_{14}$-aryl, $C_7$–$C_{20}$- arylalkyl or $C_7$–$C_{20}$-alkylaryl, or in which one of the radicals $R^1$ or $R^2$ can be, together with one of the radicals $R^3$ or $R^4$, an optionally mono- to tri-$C_1$–$C_4$-alkyl-, $C_1$–$C_4$-alkoxy-, $C_2$–$C_4$-acyl-, $C_2$–$C_4$-acyloxy-, phenoxy-, $C_2$–$C_8$-dialkylamino-, halo-, nitro- and cyano-substituted $C_2$–$C_{12}$-alkylene chain which may be interrupted by an ether, thioether, tertiary amino, keto, lactone, N-alkyl-substituted lactam or sulfone moiety, and in which X is an oxygen or sulfur atom, and/or a urea compound of the general formula II

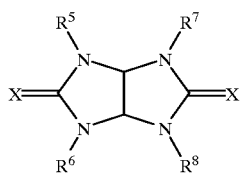

(II)

in which X has the stated meaning, and $R^5$, $R^6$, $R^7$ and $R^8$ can be identical or different and, independently of one another, have the meaning given for $R^1$ to $R^4$ and/or a compound of the general formula (III),

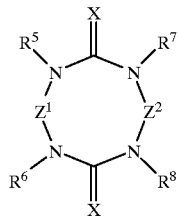

(III)

in which X, $R^5$ to $R^8$ have the abovementioned meanings and $Z^1$, $Z^2$, which may be identical or different, are an optionally mono- to tri-$C_1$–$C_4$-alkyl-, $C_1$–$C_4$-alkoxy-, $C_2$–$C_4$-acyl-, $C_2$–$C_4$-acyloxy-, phenoxy-, $C_2$–$C_8$-dialkylamino-, halo-, nitro- and/or cyano-substituted methylene, ethylene or vinylene group.

2. A process as claimed in claim 1, wherein the catalyst is N,N'-dimethylethyleneurea, N,N'-dimethylpropyleneurea, N,N,N',N'-tetrabutylurea and N,N,N',N'-tetramethylthiourea, N-chloromethyl-N'-cyanomethylpropyleneurea, N-methyl-N'-ethylpropyleneurea, 1,3-dimethyl-1,3-dihydrobenzimidazol-2-one, 1-methyl-3-phenylimidazolidine-2,4,5-trione, 1,3,4,6-tetramethyl-1,3,4,6-tetrahydroimidazo[4,5-D]imidazole-2,5-dione and 4-methoxy-1-methyl-3-phenylimidazolidine-2-thione.

3. A process as claimed in claim 1, wherein from 0.0001 to 1 mol % of the urea compound is employed, based on the alcohol.

4. A process as claimed in claim 1, wherein the reaction is carried out at temperatures from −40 to 100° C. and under atmospheric pressure.

5. A process as claimed in claim 1, wherein the reaction is carried out in the presence of a solvent.

* * * * *